(12) United States Patent  (10) Patent No.: US 8,298,278 B2
Gregorich et al.  (45) Date of Patent: Oct. 30, 2012

(54) BIFURCATED STENT WITH IMPROVEMENT SECUREMENT

(75) Inventors: Daniel Gregorich, St. Louis Park, MN (US); Michael P. Meyer, Richfield, MN (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 499 days.

(21) Appl. No.: 11/369,473

(22) Filed: Mar. 7, 2006

(65) Prior Publication Data

US 2007/0213811 A1  Sep. 13, 2007

(51) Int. Cl.
*A61F 2/06* (2006.01)
(52) U.S. Cl. .................. 623/1.15; 623/1.1; 623/1.35
(58) Field of Classification Search .............. 623/1.11, 623/1.15–1.16, 1.2, 1.35, 1.1; 606/191
See application file for complete search history.

(56) References Cited

U.S. PATENT DOCUMENTS

| | | | |
|---|---|---|---|
| 4,309,994 A | 1/1982 | Grunwald |
| 4,769,005 A | 9/1988 | Ginsburg et al. |
| 4,774,949 A | 10/1988 | Fogarty |
| 4,896,670 A | 1/1990 | Crittenden |
| 4,905,667 A | 3/1990 | Foerster et al. |
| 4,994,071 A | 2/1991 | MacGregor |
| 5,342,387 A | 8/1994 | Summers |
| 5,387,235 A | 2/1995 | Chuter |
| 5,456,712 A | 10/1995 | Maginot |
| 5,476,471 A | 12/1995 | Shifrin et al. |
| 5,487,730 A | 1/1996 | Marcadis et al. |
| 5,591,228 A | 1/1997 | Edoga |
| 5,607,444 A | 3/1997 | Lam |
| 5,609,605 A | 3/1997 | Marshall et al. |
| 5,609,627 A | 3/1997 | Goicoechea et al. |
| 5,613,980 A | 3/1997 | Chauhan |
| 5,617,878 A | 4/1997 | Taheri |
| 5,632,762 A | 5/1997 | Myler |
| 5,632,763 A | 5/1997 | Glastra |
| 5,632,772 A | 5/1997 | Alcime et al. |
| 5,636,641 A | 6/1997 | Fariabi |
| 5,669,924 A | 9/1997 | Shaknovich |

(Continued)

FOREIGN PATENT DOCUMENTS

CA  2220864  7/1999

(Continued)

OTHER PUBLICATIONS

Chevalier, M.D., Bernard, "Placement of Coronary Stents in Bifurcation Lesions by the "Culotte" Technique," *The American Journal of Cardiology*, vol. 82, pp. 943-949 (Oct. 15, 1998).

Nakamura M.D., Shigeru, "Techniques for Palmaz-Schatz Stent Deployment in Lesions with a Large Side Branch," *Catheterization and Cardiovascular Diagnosis*, vol. 34, pp. 353-361 (1995).

(Continued)

*Primary Examiner* — Corrine M McDermott
*Assistant Examiner* — Mark Mashack
(74) *Attorney, Agent, or Firm* — Vidas, Arrett & Steinkraus

(57) ABSTRACT

A stent assembly includes a branch portion and a main body with a proximal main body, a contralateral main body, and a distal main body. The branch portion is in fluid communication with the main body. In the expanded state the branch portion extends at an oblique angle in relation to the longitudinal axis. The main body and the branch portion are at least partially constructed of interconnected struts. A plurality of the struts are connected one to another by a peak. The distal main body has a greater peak width to strut width ratio than does the proximal main body and contralateral main body.

8 Claims, 5 Drawing Sheets

U.S. PATENT DOCUMENTS

| | | | |
|---|---|---|---|
| 5,669,932 | A | 9/1997 | Fischell et al. |
| 5,676,697 | A | 10/1997 | McDonald |
| 5,683,450 | A | 11/1997 | Goicoechea et al. |
| 5,697,971 | A | 12/1997 | Fischell et al. |
| 5,707,348 | A | 1/1998 | Krogh |
| 5,709,713 | A | 1/1998 | Evans et al. |
| 5,720,735 | A | 2/1998 | Dorros |
| 5,749,825 | A | 5/1998 | Fischell et al. |
| 5,749,890 | A | 5/1998 | Shaknovich |
| 5,755,734 | A | 5/1998 | Richter et al. |
| 5,755,735 | A | 5/1998 | Richter et al. |
| 5,755,771 | A | 5/1998 | Penn et al. |
| 5,755,773 | A | 5/1998 | Evans et al. |
| 5,755,778 | A | 5/1998 | Kleshinski |
| 5,782,906 | A | 7/1998 | Marshall et al. |
| 5,824,036 | A | 10/1998 | Lauterjung |
| 5,824,040 | A | 10/1998 | Cox et al. |
| 5,827,320 | A | 10/1998 | Richter et al. |
| 5,851,464 | A | 12/1998 | Davila et al. |
| 5,868,777 | A | 2/1999 | Lam |
| 5,893,887 | A | 4/1999 | Jayaraman |
| 5,906,640 | A | 5/1999 | Penn et al. |
| 5,922,020 | A * | 7/1999 | Klein et al. ................. 623/1.15 |
| 5,961,548 | A | 10/1999 | Shmulewitz |
| 5,972,017 | A | 10/1999 | Berg et al. |
| 6,013,054 | A | 1/2000 | Jiun Yan |
| 6,013,091 | A | 1/2000 | Ley et al. |
| 6,017,324 | A | 1/2000 | Tu et al. |
| 6,017,363 | A | 1/2000 | Hojeibane |
| 6,030,414 | A | 2/2000 | Taheri |
| 6,033,433 | A | 3/2000 | Ehr et al. |
| 6,033,434 | A | 3/2000 | Borghi |
| 6,033,435 | A | 3/2000 | Penn et al. |
| 6,048,361 | A | 4/2000 | Von Oepen |
| 6,056,775 | A | 5/2000 | Borghi et al. |
| 6,059,824 | A | 5/2000 | Taheri |
| 6,068,655 | A | 5/2000 | Seguin et al. |
| 6,086,611 | A | 7/2000 | Duffy et al. |
| 6,093,203 | A | 7/2000 | Uflacker |
| 6,096,073 | A | 8/2000 | Webster et al. |
| 6,099,497 | A | 8/2000 | Adams et al. |
| 6,113,579 | A | 9/2000 | Eidenschink et al. |
| 6,117,117 | A | 9/2000 | Mauch |
| 6,117,156 | A | 9/2000 | Richter et al. |
| 6,129,738 | A | 10/2000 | Lashinski et al. |
| 6,129,754 | A | 10/2000 | Kanesaka et al. |
| 6,142,973 | A | 11/2000 | Carleton et al. |
| 6,143,002 | A | 11/2000 | Vietmeier |
| 6,159,238 | A | 12/2000 | Killion et al. |
| 6,165,195 | A | 12/2000 | Wilson et al. |
| 6,168,621 | B1 | 1/2001 | Vrba |
| 6,183,509 | B1 | 2/2001 | Dibie |
| 6,190,353 | B1 | 2/2001 | Makower et al. |
| 6,203,568 | B1 | 3/2001 | Lombardi et al. |
| 6,203,569 | B1 * | 3/2001 | Wijay ........................ 623/1.15 |
| 6,210,380 | B1 | 4/2001 | Mauch |
| 6,210,429 | B1 | 4/2001 | Vardi et al. |
| 6,210,433 | B1 | 4/2001 | Larre |
| 6,254,593 | B1 | 7/2001 | Wilson |
| 6,258,115 | B1 | 7/2001 | Dubrul |
| 6,258,116 | B1 | 7/2001 | Hojeibane |
| 6,261,305 | B1 | 7/2001 | Marotta et al. |
| 6,261,316 | B1 | 7/2001 | Shaolian et al. |
| 6,264,662 | B1 | 7/2001 | Lauterjung |
| 6,264,686 | B1 | 7/2001 | Rieu et al. |
| 6,290,673 | B1 | 9/2001 | Shanley |
| 6,293,968 | B1 | 9/2001 | Taheri |
| 6,325,822 | B1 | 12/2001 | Chouinard et al. |
| 6,325,826 | B1 | 12/2001 | Vardi et al. |
| 6,334,864 | B1 | 1/2002 | Amplatz et al. |
| 6,334,870 | B1 | 1/2002 | Ehr et al. |
| 6,346,089 | B1 | 2/2002 | Dibie |
| 6,355,060 | B1 | 3/2002 | Lenker et al. |
| 6,361,544 | B1 | 3/2002 | Wilson et al. |
| 6,361,555 | B1 | 3/2002 | Wilson |
| 6,383,213 | B2 | 5/2002 | Wilson et al. |
| 6,395,018 | B1 | 5/2002 | Castaneda |
| 6,416,543 | B1 * | 7/2002 | Hilaire et al. ................ 623/1.16 |
| 6,436,104 | B2 | 8/2002 | Hojeibane |
| 6,436,134 | B2 | 8/2002 | Richter et al. |
| 6,508,836 | B2 | 1/2003 | Wilson et al. |
| 6,517,558 | B2 | 2/2003 | Gittings et al. |
| 6,520,988 | B1 | 2/2003 | Colombo et al. |
| 6,540,774 | B1 * | 4/2003 | Cox ............................. 623/1.15 |
| 6,540,779 | B2 | 4/2003 | Richter et al. |
| 6,579,309 | B1 | 6/2003 | Loos et al. |
| 6,579,312 | B2 | 6/2003 | Wilson et al. |
| 6,582,394 | B1 | 6/2003 | Reiss et al. |
| 6,596,020 | B2 | 7/2003 | Vardi et al. |
| 6,599,315 | B2 | 7/2003 | Wilson |
| 6,599,316 | B2 | 7/2003 | Vardi et al. |
| 6,645,242 | B1 | 11/2003 | Quinn |
| 6,689,156 | B1 | 2/2004 | Davidson et al. |
| 6,692,483 | B2 | 2/2004 | Vardi et al. |
| 6,695,877 | B2 | 2/2004 | Brucker et al. |
| 6,706,062 | B2 | 3/2004 | Vardi et al. |
| 6,749,628 | B1 | 6/2004 | Cho et al. |
| 6,776,793 | B2 | 8/2004 | Brown et al. |
| 6,811,566 | B1 | 11/2004 | Penn et al. |
| 6,835,203 | B1 * | 12/2004 | Vardi et al. ................... 623/1.34 |
| 6,852,124 | B2 * | 2/2005 | Cox et al. ..................... 623/1.15 |
| 6,858,038 | B2 | 2/2005 | Heuser |
| 6,884,258 | B2 | 4/2005 | Vardi et al. |
| 6,896,699 | B2 | 5/2005 | Wilson et al. |
| 6,932,837 | B2 | 8/2005 | Amplatz et al. |
| 6,955,687 | B2 | 10/2005 | Richter et al. |
| 6,955,688 | B2 | 10/2005 | Wilson et al. |
| 6,962,602 | B2 | 11/2005 | Vardi et al. |
| 7,018,400 | B2 | 3/2006 | Lashinski et al. |
| 7,056,323 | B2 | 6/2006 | Mareiro et al. |
| 7,060,091 | B2 | 6/2006 | Killion et al. |
| 2001/0003161 | A1 | 6/2001 | Vardi et al. |
| 2001/0004706 | A1 | 6/2001 | Hojeibane |
| 2001/0004707 | A1 | 6/2001 | Dereume et al. |
| 2001/0012927 | A1 | 8/2001 | Mauch |
| 2001/0016766 | A1 | 8/2001 | Vardi et al. |
| 2001/0016767 | A1 | 8/2001 | Wilson et al. |
| 2001/0016768 | A1 | 8/2001 | Wilson et al. |
| 2001/0025195 | A1 | 9/2001 | Shaolian et al. |
| 2001/0027291 | A1 | 10/2001 | Shanley |
| 2001/0027338 | A1 | 10/2001 | Greenberg |
| 2001/0029396 | A1 | 10/2001 | Wilson et al. |
| 2001/0037116 | A1 | 11/2001 | Wilson et al. |
| 2001/0037138 | A1 | 11/2001 | Wilson et al. |
| 2001/0039448 | A1 | 11/2001 | Dibie |
| 2001/0049552 | A1 | 12/2001 | Richter et al. |
| 2001/0056297 | A1 | 12/2001 | Hojeibane |
| 2002/0013618 | A1 | 1/2002 | Marotta et al. |
| 2002/0013619 | A1 | 1/2002 | Shanley |
| 2002/0022874 | A1 | 2/2002 | Wilson |
| 2002/0026232 | A1 | 2/2002 | Marotta et al. |
| 2002/0035392 | A1 | 3/2002 | Wilson |
| 2002/0042650 | A1 | 4/2002 | Vardi et al. |
| 2002/0052648 | A1 | 5/2002 | McGuckin, Jr. et al. |
| 2002/0072790 | A1 | 6/2002 | McGuckin, Jr. et al. |
| 2002/0095140 | A1 * | 7/2002 | Lootz et al. ..................... 606/1 |
| 2002/0111675 | A1 | 8/2002 | Wilson |
| 2002/0156516 | A1 | 10/2002 | Vardi et al. |
| 2002/0156517 | A1 | 10/2002 | Perouse |
| 2002/0165604 | A1 | 11/2002 | Shanley |
| 2002/0173835 | A1 | 11/2002 | Bourang et al. |
| 2002/0173840 | A1 | 11/2002 | Brucker et al. |
| 2002/0183763 | A1 | 12/2002 | Callol et al. |
| 2002/0193872 | A1 | 12/2002 | Trout, III et al. |
| 2002/0193873 | A1 | 12/2002 | Brucker et al. |
| 2003/0009209 | A1 | 1/2003 | Hojeibane |
| 2003/0028233 | A1 | 2/2003 | Vardi et al. |
| 2003/0050688 | A1 | 3/2003 | Fischell et al. |
| 2003/0055378 | A1 | 3/2003 | Wang et al. |
| 2003/0055483 | A1 | 3/2003 | Gumm |
| 2003/0074047 | A1 | 4/2003 | Richter |
| 2003/0093109 | A1 | 5/2003 | Mauch |
| 2003/0097169 | A1 | 5/2003 | Brucker |
| 2003/0114912 | A1 | 6/2003 | Sequin et al. |
| 2003/0125791 | A1 | 7/2003 | Sequin et al. |
| 2003/0125802 | A1 | 7/2003 | Callol et al. |
| 2003/0135259 | A1 | 7/2003 | Simso |

| | | |
|---|---|---|
| 2003/0181923 A1 | 9/2003 | Vardi |
| 2003/0195606 A1 | 10/2003 | Davidson et al. |
| 2004/0002753 A1* | 1/2004 | Burgermeister et al. ..... 623/1.15 |
| 2004/0006381 A1 | 1/2004 | Sequin et al. |
| 2004/0015227 A1 | 1/2004 | Vardi et al. |
| 2004/0044396 A1 | 3/2004 | Clerc et al. |
| 2004/0059406 A1 | 3/2004 | Cully et al. |
| 2004/0088007 A1 | 5/2004 | Eidenschink |
| 2004/0117003 A1 | 6/2004 | Ouriel et al. |
| 2004/0133268 A1 | 7/2004 | Davidson et al. |
| 2004/0138732 A1 | 7/2004 | Suhr et al. |
| 2004/0138737 A1 | 7/2004 | Davidson et al. |
| 2004/0148006 A1 | 7/2004 | Davidson et al. |
| 2004/0172121 A1 | 9/2004 | Eidenschink et al. |
| 2004/0186560 A1 | 9/2004 | Alt |
| 2004/0225345 A1 | 11/2004 | Fischell et al. |
| 2004/0267352 A1 | 12/2004 | Davidson et al. |
| 2005/0004656 A1 | 1/2005 | Das |
| 2005/0010278 A1 | 1/2005 | Vardi et al. |
| 2005/0015108 A1 | 1/2005 | Williams et al. |
| 2005/0015135 A1 | 1/2005 | Shanley |
| 2005/0060027 A1 | 3/2005 | Khenansho et al. |
| 2005/0096726 A1 | 5/2005 | Sequin et al. |
| 2005/0102021 A1 | 5/2005 | Osborne |
| 2005/0102023 A1 | 5/2005 | Yadin et al. |
| 2005/0119731 A1 | 6/2005 | Brucker et al. |
| 2005/0125076 A1 | 6/2005 | Ginn |
| 2005/0131526 A1 | 6/2005 | Wong |
| 2005/0149161 A1 | 7/2005 | Eidenschink et al. |
| 2005/0154442 A1 | 7/2005 | Eidenschink et al. |
| 2005/0154444 A1 | 7/2005 | Quadri |
| 2005/0183259 A1 | 8/2005 | Eidenschink et al. |
| 2005/0209673 A1 | 9/2005 | Shaked |
| 2005/0228483 A1 | 10/2005 | Kaplan et al. |
| 2005/0273157 A1* | 12/2005 | Pinchasik ............ 623/1.15 |
| 2006/0030924 A1* | 2/2006 | Van Der Leest et al. .... 623/1.11 |
| 2006/0036315 A1 | 2/2006 | Yadin et al. |
| 2006/0041303 A1 | 2/2006 | Israel |
| 2006/0079956 A1 | 4/2006 | Eigler et al. |
| 2006/0173528 A1 | 8/2006 | Feld et al. |
| 2006/0271152 A1* | 11/2006 | Hilaire et al. ............ 623/1.11 |
| 2006/0287707 A1* | 12/2006 | Roeder et al. ............ 623/1.15 |
| 2007/0073376 A1 | 3/2007 | Krolik et al. |
| 2008/0132994 A1* | 6/2008 | Burgermeister et al. .... 623/1.15 |

FOREIGN PATENT DOCUMENTS

| | | |
|---|---|---|
| DE | 9014845 | 2/1991 |
| DE | 29701758 | 3/1997 |
| DE | 29701883 | 5/1997 |
| EP | 0479730 | 10/1991 |
| EP | 0751752 | 1/1997 |
| EP | 0783873 | 7/1997 |
| EP | 0804907 | 11/1997 |
| EP | 0479557 | 7/1998 |
| EP | 0876805 | 11/1998 |
| EP | 0880949 | 12/1998 |
| EP | 0891751 | 1/1999 |
| EP | 0 895 759 | 2/1999 |
| EP | 0904745 | 3/1999 |
| EP | 0937442 | 8/1999 |
| EP | 0347023 | 12/1999 |
| EP | 1031328 | 8/2000 |
| EP | 1031329 | 8/2000 |
| EP | 0883384 | 12/2000 |
| EP | 0862392 | 8/2001 |
| EP | 0808140 | 12/2001 |
| EP | 0884028 | 2/2002 |
| EP | 1 190 685 | 3/2002 |
| EP | 0897700 | 7/2002 |
| EP | 0684022 | 2/2004 |
| EP | 1157674 | 7/2005 |
| EP | 1031330 | 11/2005 |
| EP | 1070513 | 6/2006 |
| FR | 2678508 | 1/1993 |
| FR | 2740346 | 10/1995 |
| FR | 2756173 | 11/1996 |
| GB | 2337002 | 5/1998 |
| WO | 88/06026 | 8/1988 |
| WO | 95/21592 | 8/1995 |
| WO | 96/29955 | 10/1996 |
| WO | 96/34580 | 11/1996 |
| WO | 96/41592 | 12/1996 |
| WO | 97/07752 | 3/1997 |
| WO | 97/15346 | 5/1997 |
| WO | 97/16217 | 5/1997 |
| WO | 97/26936 | 7/1997 |
| WO | 97/41803 | 11/1997 |
| WO | 97/45073 | 12/1997 |
| WO | 97/46174 | 12/1997 |
| WO | 98/19628 | 5/1998 |
| WO | 98/36709 | 8/1998 |
| WO | 98/37833 | 9/1998 |
| WO | 98/47447 | 10/1998 |
| WO | 98/48879 | 11/1998 |
| WO | 99/03426 | 1/1999 |
| WO | 99/04726 | 2/1999 |
| WO | 99/15103 | 4/1999 |
| WO | 99/15109 | 4/1999 |
| WO | 99/24104 | 5/1999 |
| WO | 99/34749 | 7/1999 |
| WO | 99/36002 | 7/1999 |
| WO | 99/36015 | 7/1999 |
| WO | 99/44539 | 9/1999 |
| WO | 99/56661 | 11/1999 |
| WO | 99/65419 | 12/1999 |
| WO | 00/07523 | 2/2000 |
| WO | 00/10489 | 3/2000 |
| WO | 00/16719 | 3/2000 |
| WO | 00/27307 | 5/2000 |
| WO | 00/27463 | 5/2000 |
| WO | 00/28922 | 5/2000 |
| WO | 01/45594 | 6/2000 |
| WO | 00/44307 | 8/2000 |
| WO | 00/44309 | 8/2000 |
| WO | 00/47134 | 8/2000 |
| WO | 00/48531 | 8/2000 |
| WO | 00/49951 | 8/2000 |
| WO | 00/51523 | 9/2000 |
| WO | 00/57813 | 10/2000 |
| WO | 00/67673 | 11/2000 |
| WO | 00/71055 | 11/2000 |
| WO | WO 00/71054 | 11/2000 |
| WO | 00/74595 | 12/2000 |
| WO | 01/21095 | 3/2001 |
| WO | 01/21109 | 3/2001 |
| WO | 01/21244 | 3/2001 |
| WO | 01/35715 | 5/2001 |
| WO | 01/35863 | 5/2001 |
| WO | 01/39697 | 6/2001 |
| WO | 01/39699 | 6/2001 |
| WO | 01/41677 | 6/2001 |
| WO | 01/43665 | 6/2001 |
| WO | 01/43809 | 6/2001 |
| WO | 01/45785 | 6/2001 |
| WO | 01/49342 | 7/2001 |
| WO | 01/54621 | 8/2001 |
| WO | 01/54622 | 8/2001 |
| WO | 01/58385 | 8/2001 |
| WO | 01/60284 | 8/2001 |
| WO | 01/70294 | 9/2001 |
| WO | 01/70299 | 9/2001 |
| WO | 01/74273 | 10/2001 |
| WO | 01/89409 | 11/2001 |
| WO | 02/00138 | 1/2002 |
| WO | 02/053066 | 7/2002 |
| WO | 02/068012 | 9/2002 |
| WO | WO 03/007842 | 1/2003 |
| WO | 03/055414 | 7/2003 |
| WO | 03/063924 | 8/2003 |
| WO | 2004/026174 | 4/2004 |
| WO | 2004/026180 | 4/2004 |
| WO | 2005/009295 | 2/2005 |
| WO | 2005/014077 | 2/2005 |
| WO | 2006/028925 | 3/2006 |

OTHER PUBLICATIONS

Caputo, Ronald P., "Stent Jail: A Minimum-Security Prison," *The American Journal of Cardiology*, vol. 77, pp. 1226-1230 (Jun. 1, 1996).

Colombo, M.D., Antonio, ""Kissing" Stent for Bifurcational Coronary Lesion," *Catheterization and Cardiovascular Diagnosis*, vol. 30, pp. 327-330 (Dec. 1993).

Carrie, M.D., Didier, ""T"-Shaped Stent Placement: A Technique for the Treatment of Dissected Bifurcation Lesions," *Catheterization and Cardiovascular Diagnosis*, vol. 37, pp. 311-313 (Mar. 1996).

Katoh, M.D., Osamu, "New Double Wire Technique to Stent Ostial Lesions," *Catheterization and Cardiovascular Diagnosis*, vol. 40, pp. 400-402 (Apr. 1997).

Lewis, M.D., Bruce E., "Acute procedural results in the treatment of 30 coronary artery bifurcation lesions with a double-wire atherectomy technique for side-branch protection," *American Heart Journal*, vol. 127:6, pp. 1600-1607 (Jun. 1994).

Yamashita, M.D.,PhD., Takehiro, "Bifurcation Lesions: Two Stents Versus One Stent—Immediate and Follow-up Results," *Journal of the American College of Cardiology*, vol. 35:5, pp. 1145-1151 (Apr. 2000).

Satler, M.D., Lowell F., "Bifurcation Disease: To Treat or Not to Treat," *Catheterization and Cardiovascular Interventions*, vol. 50, pp. 411-412 (2000).

U.S. Appl. No. 09/325,996, filed Jun. 4, 1999, Vardi et al.
U.S. Appl. No. 09/614,472, filed Jul. 11, 2000, Davidson et al.
U.S. Appl. No. 09/663,111, filed Sep. 15, 2000, Davidson et al.

* cited by examiner

BIFURCATED STENT WITH IMPROVEMENT SECUREMENT

CROSS-REFERENCE TO RELATED APPLICATIONS

Not Applicable

STATEMENT REGARDING FEDERALLY SPONSORED RESEARCH

Not Applicable

FIELD OF THE INVENTION

In some embodiments this invention relates to implantable medical devices, their manufacture, and methods of use. Some embodiments are directed to delivery systems, such as catheter systems of all types, which are utilized in the delivery of such devices.

BACKGROUND OF THE INVENTION

A stent is a medical device introduced to a body lumen and is well known in the art. Typically, a stent is implanted in a blood vessel at the site of a stenosis or aneurysm endoluminally, i.e. by so-called "minimally invasive techniques" in which the stent in a radially reduced configuration, optionally restrained in a radially compressed configuration by a sheath and/or catheter, is delivered by a stent delivery system or "introducer" to the site where it is required. The introducer may enter the body from an access location outside the body, such as through the patient's skin, or by a "cut down" technique in which the entry blood vessel is exposed by minor surgical means.

Stents, grafts, stent-grafts, vena cava filters, expandable frameworks, and similar implantable medical devices, collectively referred to hereinafter as stents, are radially expandable endoprostheses which are typically intravascular implants capable of being implanted transluminally and enlarged radially after being introduced percutaneously. Stents may be implanted in a variety of body lumens or vessels such as within the vascular system, urinary tracts, bile ducts, fallopian tubes, coronary vessels, secondary vessels, etc. Stents may be used to reinforce body vessels and to prevent restenosis following angioplasty in the vascular system. They may be self-expanding, expanded by an internal radial force, such as when mounted on a balloon, or a combination of self-expanding and balloon expandable (hybrid expandable).

Stents may be created by methods including cutting or etching a design from a tubular stock, from a flat sheet which is cut or etched and which is subsequently rolled or from one or more interwoven wires or braids.

Within the vasculature it is not uncommon for stenoses to form at a vessel bifurcation. A bifurcation is an area of the vasculature or other portion of the body where a first (or parent) vessel is bifurcated into two or more branch vessels. Where a stenotic lesion or lesions form at such a bifurcation, the lesion(s) can affect only one of the vessels (i.e., either of the branch vessels or the parent vessel) two of the vessels, or all three vessels. Many prior art stents however are not wholly satisfactory for use where the site of desired application of the stent is juxtaposed or extends across a bifurcation in an artery or vein such, for example, as the bifurcation in the mammalian aortic artery into the common iliac arteries.

The art referred to and/or described above is not intended to constitute an admission that any patent, publication or other information referred to herein is "prior art" with respect to this invention.

All US patents and applications and all other published documents mentioned anywhere in this application are incorporated herein by reference in their entirety.

Without limiting the scope of the invention a brief summary of some of the claimed embodiments of the invention is set forth below. Additional details of the summarized embodiments of the invention and/or additional embodiments of the invention may be found in the Detailed Description of the Invention below.

A brief abstract of the technical disclosure in the specification is provided as well only for the purposes of complying with 37 C.F.R. 1.72. The abstract is not intended to be used for interpreting the scope of the claims.

BRIEF SUMMARY OF THE INVENTION

In at least one embodiment, the invention is directed to a stent assembly having a main body with a proximal main body, a contralateral main body, and a distal main body at least partially constructed of interconnected struts connected one to another by a peak wherein the distal main body has a greater peak width to strut width ratio than does the proximal main body and contralateral main body. In at least one embodiment, a branch portion may be in fluid communication with the main body such that in the expanded state the branch portion extends at an oblique angle in relation to the longitudinal axis. In at least one embodiment the branch portion extends from the contralateral main body.

In at least one embodiment, the peak width to strut width ratio of the distal main body is about 3 to 1. Other ratios include 1.1:1, 1.25:1, 1.5:1.75:1, 2:1, 2.5:1, 3.5:1, etc.

In at least one embodiment, the peaks in the distal main body have a greater strain concentration than does the rest of the stent.

In at least one embodiment, the stent assembly may be disposed about at least one catheter balloon.

In at least one embodiment, the branch portion may be deployed using a second balloon.

In at least one embodiment, the distal main body may comprise at least one third of the length of the stent assembly.

In at least one embodiment, the struts of the distal main body may be narrower than the struts of the rest of the stent.

In at least one embodiment, the peaks of the distal main body may be wider than the peaks of the rest of the stent.

In at least one embodiment, the stent assembly may be secured to the catheter only in the distal main body.

In at least one embodiment, the stent assembly may be secured to a catheter in at least one of the proximal main body, the contralateral main body, and the distal main body.

In at least one embodiment, the stent assembly may comprise a plurality of annular bands having a serpentine configuration.

In at least one embodiment, the annular bands of the distal main body may have a smaller number of peaks than the annular bands of the proximal main body and the contralateral main body.

In at least one embodiment, the proximal main body, the contralateral main body, and the branch portion may have the substantially same peak width to strut width ratio.

In at least one embodiment, the peaks in the distal main body are at least twice as wide as the struts of the distal main body.

In at least one embodiment of the invention a method of securing a stent assembly to a catheter balloon comprises providing a stent assembly as described above, disposing the stent assembly about a catheter balloon and a branch balloon, and securing the peaks and/or struts of the distal main body of the stent assembly to the catheter balloon. In at least one embodiment, the struts and peaks of the distal main body may be secured to the catheter balloon by plastically deforming the struts and peaks. Plastically deforming the stent struts and/or peaks may prevent them from elastically recoiling away from the balloon. By preventing this recoil, the mechanical interaction between the stent struts/peaks and balloon material may resist movement of the stent in relation to the balloon when an external force is applied.

These and other embodiments which characterize the invention are pointed out with particularity in the claims annexed hereto and forming a part hereof. However, for further understanding of the invention, its advantages and objectives obtained by its use, reference should be made to the drawings which form a further part hereof and the accompanying descriptive matter, in which there is illustrated and described an embodiments of the invention.

BRIEF DESCRIPTION OF THE SEVERAL VIEWS OF THE DRAWING(S)

A detailed description of the invention is hereafter described with specific reference being made to the drawings.

DETALED DESCRIPTION OF THE INVENTION

Figure 1:
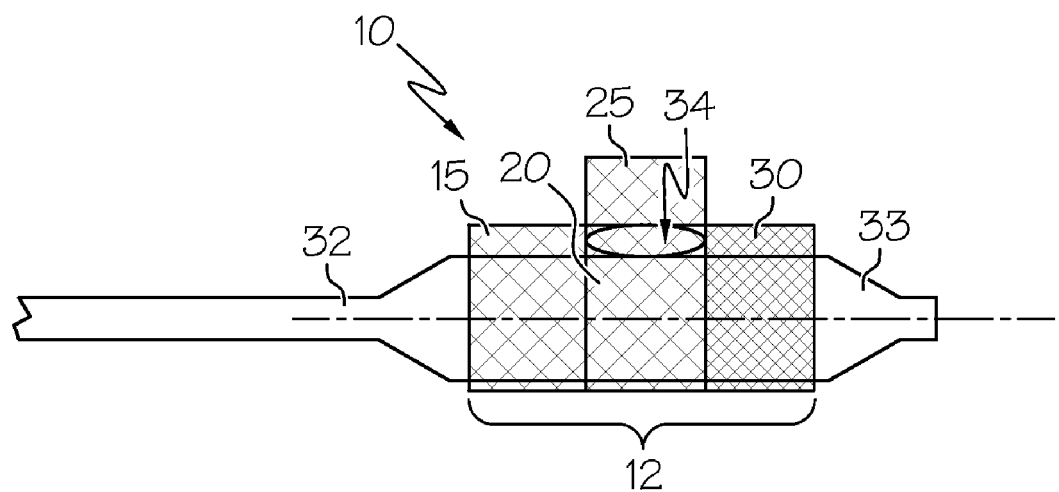
FIG. 1 is a side view of the bifurcated stent disposed about a catheter balloon.

While this invention may be embodied in many different forms, there are described in detail herein specific embodiments of the invention. This description is an exemplification of the principles of the invention and is not intended to limit the invention to the particular embodiments illustrated.

For the purposes of this disclosure, like reference numerals in the figures shall refer to like features unless otherwise indicated.

In FIG. 1 stent assembly 10 has a main body 12 and a branch portion 25 with a longitudinal axis 32 passing through the main body 12. The main body includes a proximal main body 15, a contralateral main body 20, a distal main body 30, and a branch portion 25. In at least one embodiment the branch portion 25 extends from the contralateral main body 20. The stent assembly 10 may be expanded using balloons 33 and 34. The balloons may expand simultaneously or one may expand before the other. The branch portion 25 may comprise a petal region. In at least one embodiment, the petals comprise a single members that when expanded extend obliquely out from the main body 12 of the stent. The branch portion may also comprise portions which extend obliquely that are formed from interconnected bands.

In some embodiments as shown in FIG. 1, the distal main body 30 is about one third of the length of the main body 12. In some embodiments, the distal main body 30, the contralateral main body 20, and the proximal main body 15 each comprise about a third of the length of the main body 12; however they may comprise many different percentages of the total main body length as well.

Figure 2:
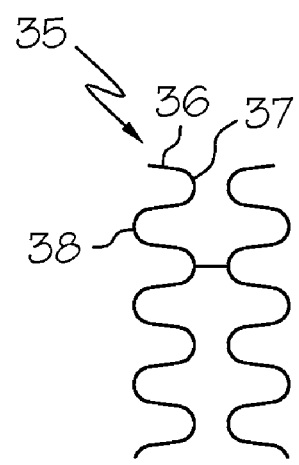
FIG. 2 is a side view of a pair of serpentine bands having peaks.

The main body 12 may be constructed of interconnected bands. FIG. 2 illustrates two such bands 35. Though only two bands are shown many more interconnected bands 35 may be used. Each interconnected band 35 as shown includes a plurality of interconnected struts 36. The interconnected struts 36 may be connected by peak portions 37 or valley portions 38.

Figure 3A:
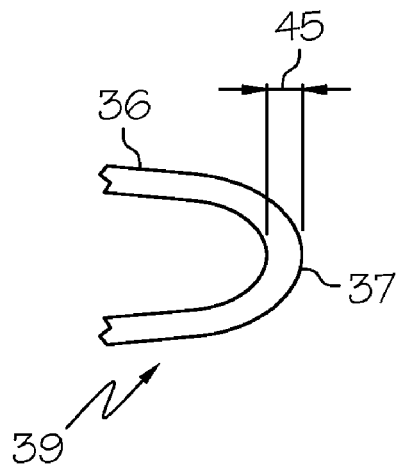
FIG. 3a is a side view of a peak in the proximal main body.
Figure 3B:
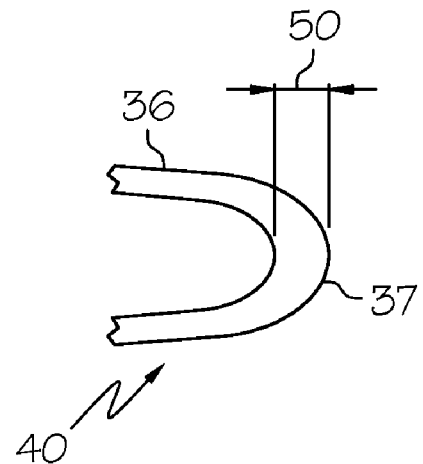
FIG. 3b is a side view of a peak in the distal main body.

In FIGS. 3a and 3b an enlarged segment 39 of a proximal band 35 is shown juxtaposed with an enlarged segment 40 of a distal band 35. The distal band peak 37 has a greater peak width 50 than the peak width 45 of segment 39 while the strut widths of each segment are similar. The greater peak width to strut width ratio of segment 40 provides increased strain concentration resulting in higher securement.

The higher securement of the peak portions 37 in the distal main body 30 improves the securement of the entire stent assembly 10 as the securement of a bifurcated stent is dependent on the interaction between only the distal end of the stent interacting with the delivery balloon. In some embodiments the peak width to strut width ratio is 3 to 1. In some instances it is at least 2 to 1.

In some embodiments, the peaks in the distal main body have a width that is equal to or less than the width of the peaks in the rest of the stent. In such embodiments, the increased peak width to strut width ratio is maintained by strut widths in the distal main body that are proportionally narrower than the strut widths in the rest of the stent. In some embodiments, the stent assembly may be secured to the balloon in only the distal main body. In some embodiments, securement to the balloon is present in other parts of the stent assembly.

In some embodiments, the number of peaks in one annular band may be greater than the number of peaks in another annular band. In some embodiments, the annular bands of the distal main body have a smaller number of peaks in the annular bands than in other parts of the stent assembly.

Figure 4:
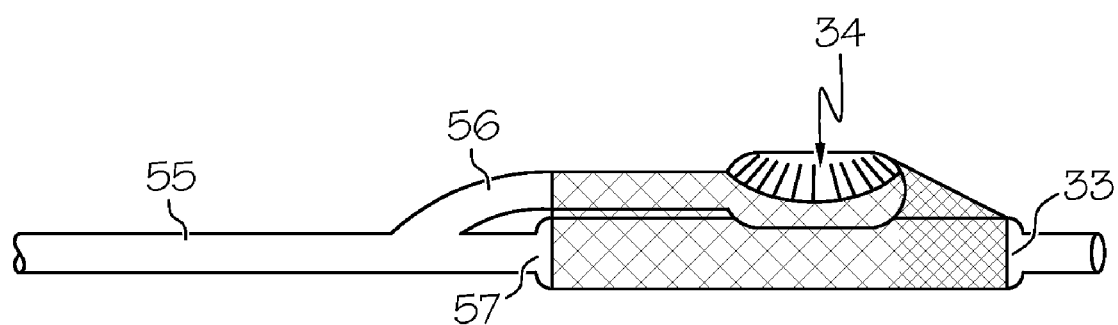
FIG. 4 is a side view of a bifurcated stent with two inflation balloons

In some embodiments as shown in FIG. 1, the second balloon 34 is in fluid communication with first balloon 33. Balloons 33 and 34 may be constructed of material different from one another such that under the same pressure one or the other balloon may inflate before the other balloon. As shown in FIG. 4, some embodiments of the invention include balloons 33 and 34 that are not directly in fluid communication. In some embodiments, as shown, the second balloon 34 shares a portion of the inflation lumen until the lumen splits in the area of a bifurcation. In some embodiments, the second balloon has an inflation lumen separate from the inflation lumen of the first balloon 33.

Figure 5:
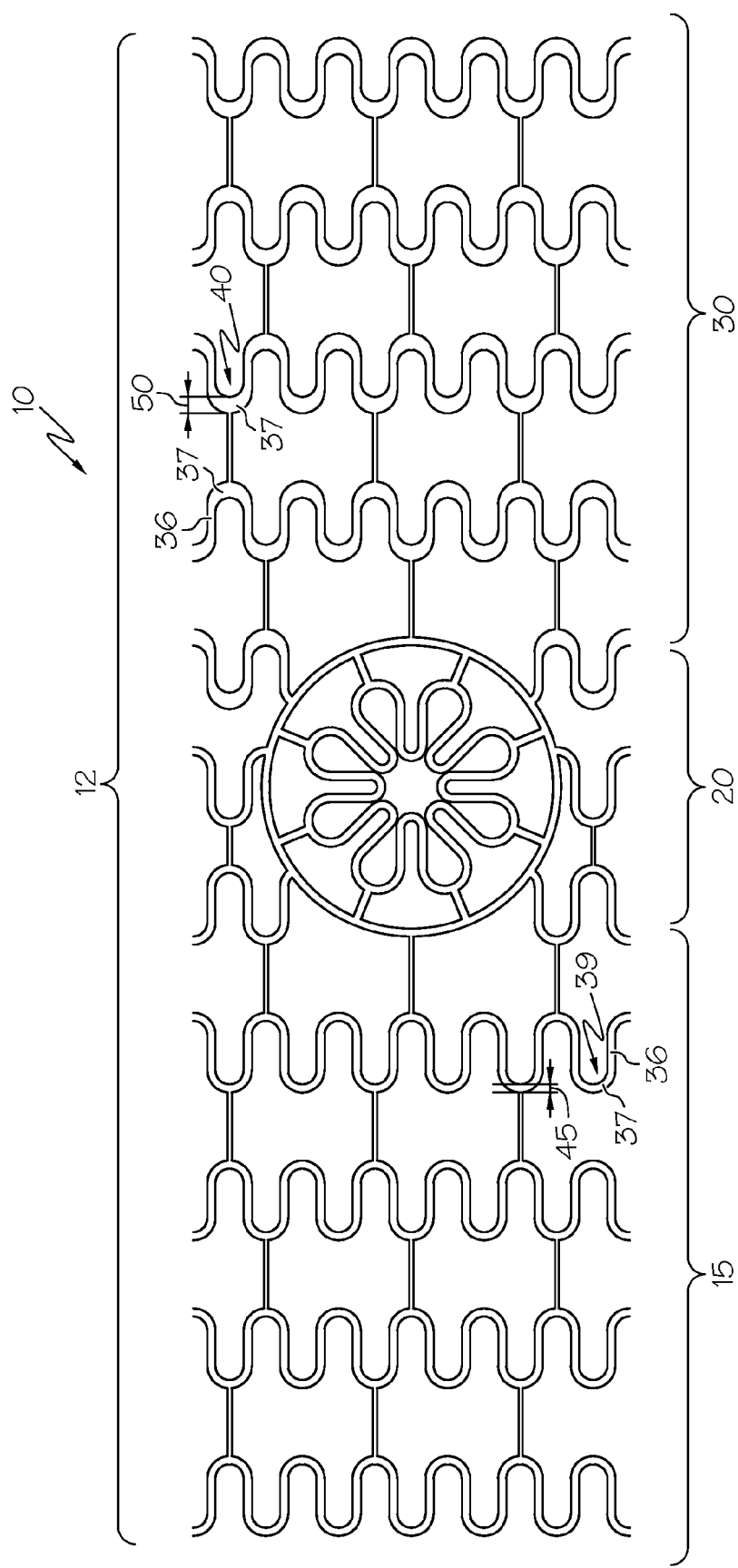
FIG. 5 is a flat view of an embodiment of the bifurcated stent depicted in FIG. 1 in an unexpanded state, in accordance with the present invention.
Figure 6:
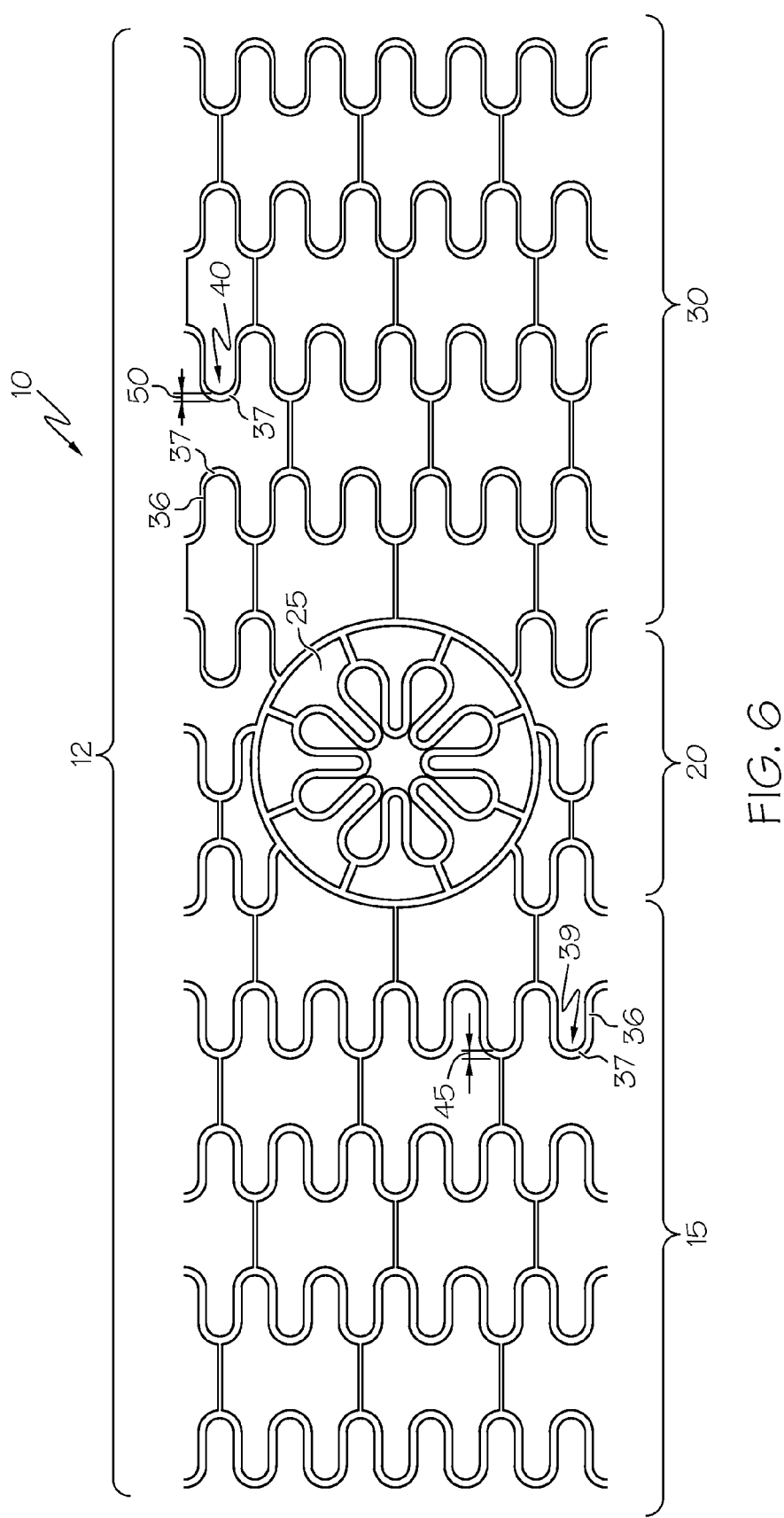
FIG. 6 is a flat view of another embodiment of the bifurcated stent depicted in FIG. 1 in an unexpanded state, in accordance with the present invention.
Figure 7:
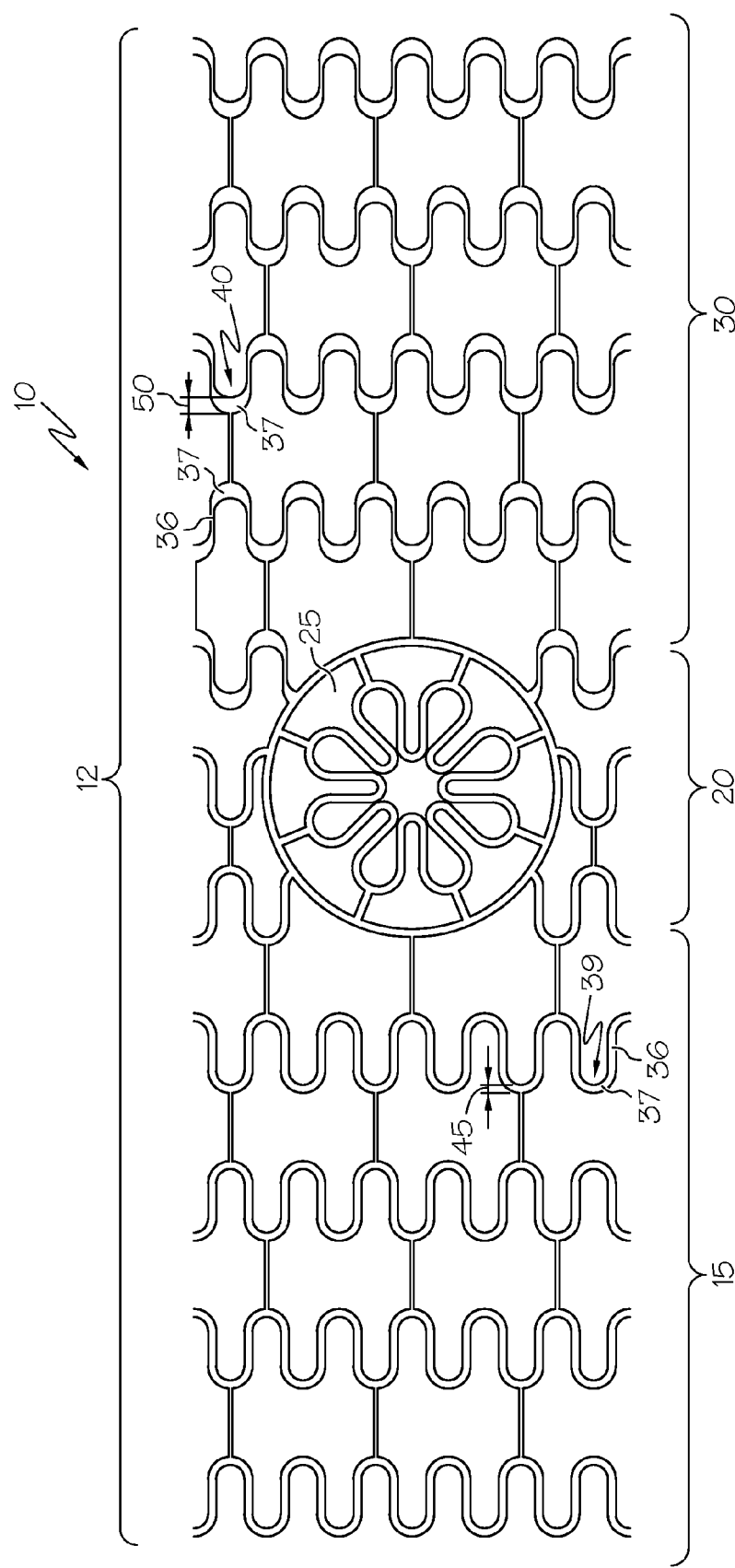
FIG. 7 is a flat view of another embodiment of a stent.

As shown in FIGS. 5-7, in some embodiments, the distal closed serpentine bands have a greater peak width than the proximal closed serpentine bands. In some embodiments, the distal closed serpentine bands have narrower struts than the proximal closed serpentine bands.

The inventive stents may be created by methods including cutting or etching a design from a tubular stock, from a flat sheet which is cut or etched and which is subsequently rolled or from one or more interwoven wires or braids. Any other suitable technique which is known in the art or which is subsequently developed may also be used to manufacture the inventive stents disclosed herein.

In some embodiments at least a portion of the stent assembly is configured to include one or more mechanisms for the delivery of a therapeutic agent. Often the agent will be in the form of a coating or other layer (or layers) of material placed on a surface region of the stent, which is adapted to be released at the site of the stent's implantation or areas adjacent thereto. The therapeutic agent can be applied in a variety of ways and can include therapeutic agent being applied in some locations more than others.

A therapeutic agent may be a drug or other pharmaceutical product such as non-genetic agents, genetic agents, cellular material, etc. Some examples of suitable non-genetic therapeutic agents include but are not limited to: anti-thrombogenic agents such as heparin, heparin derivatives, vascular cell growth promoters, growth factor inhibitors, Paclitaxel, etc. Where an agent includes a genetic therapeutic agent, such a genetic agent may include but is not limited to: DNA, RNA and their respective derivatives and/or components; hedgehog proteins, etc. Where a therapeutic agent includes cellular material, the cellular material may include but is not limited to: cells of human origin and/or non-human origin as well as their respective components and/or derivatives thereof. Where the therapeutic agent includes a polymer agent, the polymer agent may be a polystyrene-polyisobutylene-polystyrene triblock copolymer (SIBS), polyethylene oxide, silicone rubber and/or any other suitable substrate.

The inventive stents may be made from any suitable biocompatible materials including one or more polymers, one or more metals or combinations of polymer(s) and metal(s). Examples of suitable materials include biodegradable materials that are also biocompatible. By biodegradable is meant that a material will undergo breakdown or decomposition into harmless compounds as part of a normal biological process. Suitable biodegradable materials include polylactic acid, polyglycolic acid (PGA), collagen or other connective proteins or natural materials, polycaprolactone, hylauric acid, adhesive proteins, co-polymers of these materials as well as composites and combinations thereof and combinations of other biodegradable polymers. Other polymers that may be used include polyester and polycarbonate copolymers. Examples of suitable metals include, but are not limited to, stainless steel, titanium, tantalum, platinum, tungsten, gold and alloys of any of the above-mentioned metals. Examples of suitable alloys include platinum-iridium alloys, cobalt-chromium alloys including Elgiloy and Phynox, MP35N alloy and nickel-titanium alloys, for example, Nitinol.

The inventive stents may be made of shape memory materials such as superelastic Nitinol or spring steel, or may be made of materials which are plastically deformable. In the case of shape memory materials, the stent may be provided with a memorized shape and then deformed to a reduced diameter shape. The stent may restore itself to its memorized shape upon being heated to a transition temperature and having any restraints removed therefrom.

In some embodiments the stent, the delivery system or other portion of the assembly may include one or more areas, bands, coatings, members, etc. that is (are) detectable by imaging modalities such as X-Ray, MRI, ultrasound, etc. In some embodiments at least a portion of the stent and/or adjacent assembly is at least partially radiopaque.

The above disclosure is intended to be illustrative and not exhaustive. This description will suggest many variations and alternatives to one of ordinary skill in this art. The various elements shown in the individual figures and described above may be combined or modified for combination as desired. All these alternatives and variations are intended to be included within the scope of the claims where the term "comprising" means "including, but not limited to".

Further, the particular features presented in the dependent claims may be combined with each other in other manners within the scope of the invention such that the invention should be recognized as also specifically directed to other embodiments having any other possible combination of the features of the dependent claims. For instance, for purposes of claim publication, any dependent claim which follows should be taken as alternatively written in a multiple dependent form from all prior claims which possess all antecedents referenced in such dependent claim if such multiple dependent format is an accepted format within the jurisdiction (e.g. each claim depending directly from claim 1 should be alternatively taken as depending from all previous claims). In jurisdictions where multiple dependent claim formats are restricted, the following dependent claims should each be also taken as alternatively written in each singly dependent claim format which creates a dependency from a prior antecedent-possessing claim other than the specific claim listed in such dependent claim below.

This completes the description of the invention. Those skilled in the art may recognize other equivalents to the specific embodiment described herein which equivalents are intended to be encompassed by the claims attached hereto.

What is claimed is:

1. A stent comprising:
   a central portion comprising a branch portion and a contralateral main body, the contralateral main body comprising at least one partial serpentine band attached to the branch portion;
   a plurality of proximal serpentine bands located proximal to the central portion;
   a plurality of distal serpentine bands located distal to the central portion;
   each serpentine band comprising of a repeating waveform, said waveform comprising alternating struts and peaks, the distal serpentine bands having a greater peak width than the proximal serpentine bands, the distal serpentine bands having narrower struts than the proximal serpentine bands.

2. The stent assembly of claim 1 wherein a peak width to strut width ratio of at least one distal serpentine band is about 3 to 1.

3. The stent assembly of claim 1 disposed about at least one catheter balloon.

4. The stent assembly of claim 3 wherein the branch portion is deployed using a second balloon.

5. The stent assembly of claim 1 wherein the peaks of the distal serpentine bands are wider than the peaks of the rest of the stent.

6. The stent assembly of claim 1 wherein a partial serpentine band comprises a smaller peak width to strut width ratio than a distal serpentine band.

7. The stent of claim 1 wherein the distal serpentine bands have less peaks than the proximal serpentine bands.

8. The stent of claim 1, wherein the stent comprises stainless steel or nickel titanium.

* * * * *